United States Patent [19]

Montgomery, Jr. et al.

[11] 4,003,703
[45] Jan. 18, 1977

[54] METHOD OF STERILIZING USING A ROTARY DISK-BALL VALVE CONTROL SYSTEM

[75] Inventors: Robert A. G. Montgomery, Jr., Southampton; Richard Laurence Burley, Holland, both of Pa.

[73] Assignee: Environmental Tectonics Corporation, Southampton, Pa.

[22] Filed: Oct. 18, 1974

[21] Appl. No.: 515,939

[52] U.S. Cl. .................... 21/56; 21/58; 21/93; 21/104; 137/624.18
[51] Int. Cl.² .................... A61L 1/00; A61L 5/00
[58] Field of Search ............ 21/93, 103, 104, 56, 21/94, 57–59; 137/624.18, 624.2

[56] References Cited
UNITED STATES PATENTS

| | | | |
|---|---|---|---|
| 1,902,625 | 3/1933 | Dunham | 21/94 |
| 3,087,210 | 4/1963 | Neiss | 21/93 |
| 3,431,065 | 3/1969 | Schipanski | 21/94 |
| 3,436,170 | 4/1969 | Lodge | 21/94 |
| 3,454,353 | 7/1969 | Bjork | 21/103 X |
| 3,571,563 | 3/1971 | Shulz | 21/103 X |

FOREIGN PATENTS OR APPLICATIONS

| | | | |
|---|---|---|---|
| 566,736 | 1/1924 | France | 21/104 |
| 390,221 | 4/1933 | United Kingdom | 21/104 |
| 221,701 | 9/1924 | United Kingdom | 21/104 |

Primary Examiner—Morris O. Wolk
Assistant Examiner—Bradley Garris
Attorney, Agent, or Firm—Seidel, Gonda & Goldhammer

[57] ABSTRACT

A plurality of valves, including ball valves, regulates the flow of a sterilizing agent to and from a sterilizing chamber. Rotary means connected to a ball valve regulates the flow of the sterilizing agent through the valve. Driving means cause the rotary means to rotate, thereby opening or closing the ball valve at predetermined times. A plurality of switches regulate the driving means, and circuit means connected to the switching means regulate the temperature and pressure in the chamber in timed relation with the driving means. Camming means coupled to the driving means operate the switching means in timed relation with the driving means.

6 Claims, 12 Drawing Figures

SOLID LINES INDICATE MICROSWITCH CLOSED

SOLID LINES INDICATE VALVE IS OPENING
DOTTED LINES INDICATE VALVE IS CLOSING
HATCHING INDICATES VALVE FULL OPEN

METHOD OF STERILIZING USING A ROTARY DISK-BALL VALVE CONTROL SYSTEM

BACKGROUND OF THE INVENTION

The present invention relates to a sterilizer system. More particularly the present invention relates to a ball valve sterilizer system and control.

Various sterilizer systems which utilize steam as a sterilizing agent are known in the art. Typically, a steam sterilizer system is used in hospitals, chemical laboratories, biological laboratories and, in general, wherever materials must be sterilized. The present invention is not limited to sterilizer systems using steam only, it is applicable to all types of sterilizers, including gas sterilizers, low temperature sterilizers, washer sterilizers, and steam-vacuum sterilizers. For the purpose of conciseness, however, the invention is described herein in terms of a general purpose steam sterilizer. It should be understood, however, that the invention is equally applicable to sterilizers using other gases as the sterilizing agent.

As used in a hospital, a sterilizer must be capable of sterilizing at least three different types of materials, namely, fabrics such as caps, gowns, and dressings; surgical instruments; and chemical solutions. The operation of a sterilizer using steam depends upon control of the flow of steam at high pressures and temperatures. In the past, sterilizers employed poppet valves to control the steam flow. It was found that the poppet valves used in a sterilizer became defective due to articles or impurities in the steam which interfered with proper seating of the valve face on the valve seat and due to corrosion by the steam. As a result, the flow of steam could not be reliably or accurately regulated. Moreover, due to the failure of the valve to properly regulate the flow of steam, the sterilizer failed to sterilize the article or matter to be sterilized. In many areas, and especially in hospital operating rooms, this could prove to be disastrous.

BRIEF SUMMARY OF THE INVENTION

A principal advantage of the present invention is that the flow of sterilizing agent is reliably and accurately regulated by ball valves and the problem of valve failure is substantially avoided.

Another advantage of the present invention is that the valves are accurately, efficiently and reliably operated in synchronism with electrical control circuitry which determines the sequence of steps for sterilizing the matter to be sterilized.

Another advantage of the present invention is that the rotation of the ball member of a ball valve provides a continuous wiping action which maintains the valve seating clean and free of corrosion. Unlike poppet valves, the ball valve is less subject to defects from particles or impurities in the steam and is also not as subject to corrosion when used with steam or gas sterilizing systems.

Another advantage of the present invention is the means for rotating the ball valve member, which enables 360° rotation of the member. Full 360° rotation of the ball valve member is a significant advantage over prior art devices which are limited to 90° rotation, since a much cleaner wiping action is achieved.

Another advantge of the present invention is that the means for rotating the ball valve member is economical. The present invention utilizes a mechanical arrangement of program disks for operating a plurality of ball valves whereas prior art devices required individual electromechanical means to move a ball valve member back and forth through a 90° arc. These electromechanical devices are expensive since the armature of the electromechanical device is required to provide a significant force.

Briefly, in accordance with the present invention, matter, in the form of either solids or liquids, is sterilized by flowing a gaseous sterilizing agent such as steam at high temperatures into a sterilizing chamber. A plurality of valves, including ball valves, control the flow of the sterilizing agent to and from the sterilizing chamber. Each of the ball valves includes a housing and a ball valve member disposed within the housing and connected to a rotatable stem. The housing and valve member are provided with flow passages. Rotary means are mounted on the stem, and rotation of the rotary means opens and closes the ball valves by aligning the flow passages. Driving means rotate the rotary means to open and close the ball valves at predetermined times, and electrical switching means regulate the driving means. Circuit means connected to the switching means regulate the temperature and pressure of the sterilizing chamber in timed relation with the driving means, and camming means coupled to the driving means operate the switching means in timed relation with the driving means.

BRIEF DESCRIPTION OF THE DRAWINGS

For the purpose of illustrating the invention, there is shown in the drawings a form which is presently preferred; it being understood, however, that this invention is not limited to the precise arrangements and instrumentalities shown.

DETAILED DESCRIPTION OF THE INVENTION

Figure 6A:
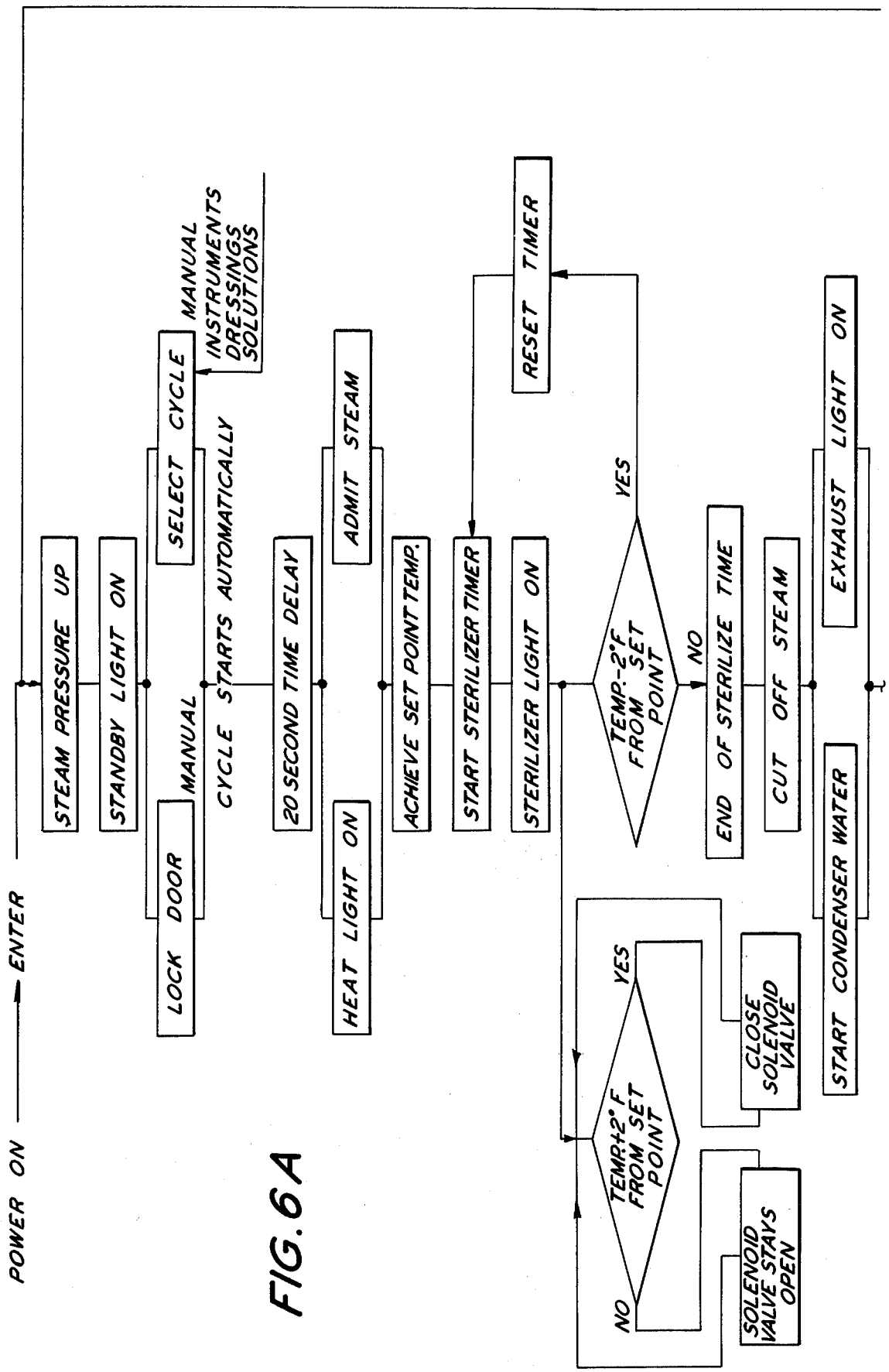
FIGS. 6A and 6B comprise a decisional flow chart representing the operational states of an apparatus in accordance with the present invention.
Figure 6B:
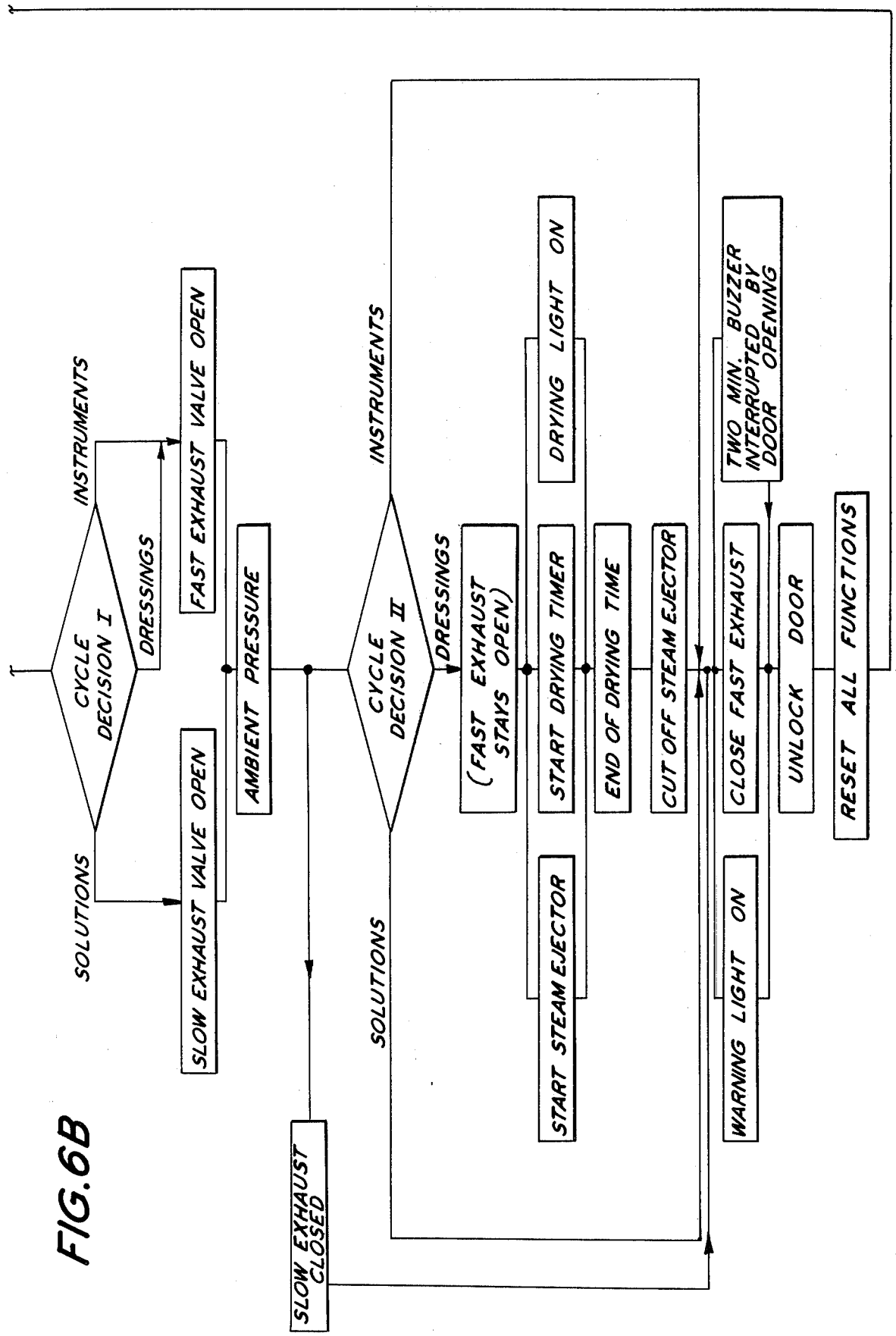

Referring to the drawings in detail, wherein like numerals indicate like elements, in FIGS. 6A and 6B there is shown a flow chart representing the sequence of decisions made during the operation of the present invention. The functions performed at each decisional block shown in FIGS. 6A and 6B correspond to the system components appearing in FIGS. 7A, 7B and 8. Accordingly, reference will be made to the latter figures in the course of describing the characteristic features of the invention as they are depicted in the flow charts in FIGS. 6A and 6B.

The operation of the system begins by monitoring the steam pressure in the piping extending from a pressure source (not shown) to the apparatus. This is accomplished by a pressure-sensitive switch 34, shown in FIGS. 7A and 8. If the steam pressure exceeds a preselected threshold value, the pressure-sensitive switch 34 closes. This is indicated by the STEAM PRESSURE UP block. When switch 34 closes, it provides a current path to manual switches 108b, 110b, and 112b. Manual switches 108b, 110b and 112b determine the mode or cycle of operation of the invention, namely, the INSTRUMENTS, DRESSINGS or SOLUTION modes represented by the SELECT CYCLE block. The cycle of operation is selected by manually depressing one of the switches 108b, 110b and 112b. The selected cycle, however, will not begin until standby light 128 goes off. Standby light 128 remains on until the chamber door (not shown) is locked.

With toggle switch 102 closed, power is applied to line 101a from power line 101. When the chamber door is open, switch 124a is closed and standby light 128 is on. Locking the chamber door opens switch 124a, de-energizing standby light 128. This is indicated by the blocks labeled LOCK DOOR and STANDBY LIGHT ON in FIG. 6A.

Pressure-sensitive switch 34 determines when the apparatus enters an operating cycle. If the steam pressure in the piping connecting the steam source to the apparatus is above the preselected threshold, switch 34 closes, supplying power to switches 108b, 110b and 112b. If the steam pressure falls below the preselected threshold, however, the system will not operate, switch 34 remaining open. The STEAM PRESSURE UP block and switch 34 may both be omitted if the steam pressure source is reliable and pressure monitoring is not required. Also, the STEAM PRESSUE UP block may be omitted if it is preferred to monitor the steam pressure by a gauge such as the chamber jacket pressure gauge 45, see FIG. 8.

Assuming that the steam pressure exceeds the preselected threshold, the apparatus is actuated by manually locking the chamber door and manually depressing one of switches 108b, 110b and 112b to select one of the three available cycles of operation. If both of the aforementioned conditions are met, that is, if the door is locked and a cycle of operation has been selected, the standby light 128 goes off and the apparatus begins to operate automatically following a fixed time delay.

Closing the chamber door provides power to time delay relay 126 through switch 124, switch 34, switch 200 and either switch 108b, 110b or 112b. Time delay relay 126 controls the operation of contacts 127. This is represented in FIG. 6A by the block labeled 20 SECOND TIME DELAY. In the preferred embodiment shown, the duration of the delay interval is 20 seconds, that is, time delay relay 126 closes contacts 127 after a 20 second delay. However, it should be apparent that delay intervals of differing durations may be used without departing from the spirit or scope of the invention. At the termination of the delay period, time delay relay 126 closes contacts 127, providing current through switch 114a to motor 120. The operation of motor 120 is described in further detail in a later portion of this disclosure.

Figure 8:
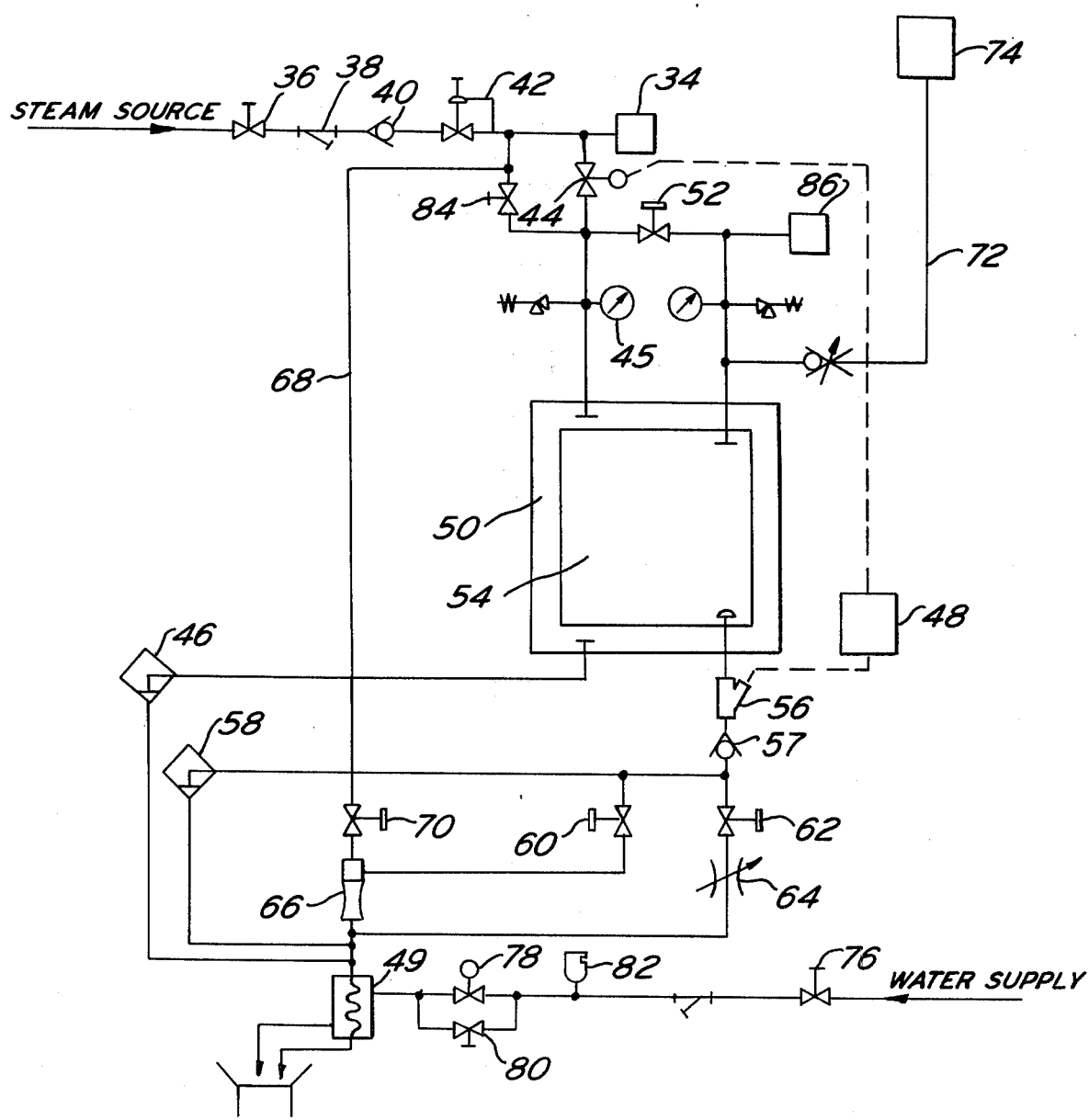
FIG. 8 is a piping diagram in accordance with the present invention.

Referring to FIG. 8, steam is admitted to chamber 54 and chamber jacket 50 through steam entry valve 44, which is a solenoid valve, until a temperature within a predetermined range of a preselected temperature (the "set point" temperature) is reached. Temperature controller and recorder 48 monitors the temperature of the steam in chamber 54 and opens and closes valve 44 in response. Steam flows through steam entry valve 44 to chamber 54 and chamber jacket 50 when valve 44 is open. Valve 44 is open when temperature-sensitive switch 104, in controller and recorder 48, closes. When terminals 106 and 134 are connected, current flows through switch 204 and light 130 is on. This segment of the system operation is represented by the parallel blocks labeled HEAT LIGHT ON and ADMIT STEAM.

As steam flows through valve 44 into chamber 54 and jacket 50, the chamber temperature falls within a predetermined range of the set point temperature. At this time, switch 51 in controller and recorder 48 disconnects terminals 106 and 134 and connects terminals 106 and 132. With terminals 106 and 132 connected, current flows to sterilizer timer 136. This is indicated by the START STERILIZER TIMER block. When sterilizer timer 136 is activated, switch 140 closes and switch 142 opens. With switch 140 closed, current flows through terminals 106 and 132 to a serilizer light 138. This is indicated by the STERILIZER LIGHT ON block. With switch 142 open, no current can flow to switch 206. The operation of switch 206 in connection with the operation cycles of the apparatus is discussed in further detail hereinafter.

While the sterilizer timer 136 is operating, temperature controller and recorder 48 regulates the temperature inside chamber 54. Specifically, as shown in the control loop containing the block marked TEMP. + 2° F. FROM SET POINT, if the temperature of chamber 54 is not more than 2° F. above the set point temperature, temperature sensitive switch 104 in controller and recorder 48 remains closed so that valve 44 remains open, admitting steam into chamber 54 and jacket 50. Should, however, the chamber temperature reach 2° F. above the set point temperature, temperature-sensitive switch 104 opens so that steam entry valve 44 closes preventing steam from entering chamber 54 and jacket 50.

Once activated, sterilizer timer 136 runs continuously, whether valve 44 opens or closes, that is, whether or not switch 104 opens or closes. But if the chamber temperature falls to 2° F. below the set point temperature, sterilizer timer 136 stops running. When the chamber temperature falls to 2° F. below the set point temperature, switch 51 reconnects terminals 106 and 134 to reset sterilizer timer 136. The resetting operation is governed by the block marked TEMP. −2° F. FROM SET POINT. From the foregoing, it can be appreciated that the operation of the sterilizer timer 136 may be intermittent depending upon the chamber temperature.

If the chamber temperature remains greater than 2° F. below the set point temperature and the sterilizer timer 136 measures one complete interval in the preferred embodiment without being reset, then motor 120 operates to cause ball valve 52 to close, see FIG. 8, thereby blocking the flow of steam from the source to chamber 54. This is indicated by the END OF STERIL- IZE TIME and CUT OFF STEAM blocks in FIG. 6A. The synchronous operation of ball valve 52 with motor 120 is described in detail hereinafter.

After steam is cut off from chamber 54 and jacket 50, the step of exhausting the steam from chamber 54 commences. This step is monitored by ambient pressure switch 86 as explained hereinafter. During the exhaust step, an exhaust light 150 is illuminated and the steam is exhausted from chamber 54 and converted to water by water condensor 49. The rapidity with which the steam is exhausted from chamber 54 varies in accordance with the type of article being sterilized as indicated in the CYCLE DECISION I loop shown in FIG. 6B. Thus, if the cycle originally selected was for either instruments or dressings, chamber 54 is exhausted quickly by opening fast exhaust ball valve 60. On the other hand, if the cycle originally selected corresponded to solutions, the slow exhaust ball valve 62 is opened and chamber 54 is exhausted slowly.

If the slow exhaust ball valve 62 is opened, chamber 54 is exhausted until ambient pressure is reached. At this point ambient pressure switch 86 closes to apply power to switch 212. Slow exhaust ball valve 62 is then closed in synchronous operation with motor 120, and it must be determined whether the apparatus should enter into a drying cycle. The synchronous operation of ball valve 62 with motor 120 is described in detail hereinafter. The drying cycle is used only if the article being sterilized is a fabric, surgical dressing, cap, gown, etc. As shown by the CYCLE DECISION II loop in FIG. 6B, a drying cycle will not be entered if the cycle originally selected was for either solutions or instruments. Assuming, however, that dressings are being sterilized, that is, that the drying cycle is entered by CYCLE DECISION II, and assuming further that fast exhaust ball valve 60 had been opened, fast exhaust ball valve 60 is maintained open as indicated by the block labeled (FAST EXHAUST STAYS OPEN). The drying timer 152 (see FIG. 7B), then, begins to measure the drying interval and drying light 154 is illuminated as indicated by the START DRYING TIMER and DRYING LIGHT ON blocks. In addition, ball valve 70 is opened when drying timer 152 is on so that steam ejector 66 starts operating, as indicated by the block labeled START STEAM EJECTOR. The steam ejector 66 receives the steam flowing through fast exhaust ball valve 60 and ejects it to condensor 49. The system continues to operate in this state without interruption until the termination of the drying interval, at which time ball valve 70 closes and steam ejector 66 is cut off. This is indicated by the block labeled CUT OFF STEAM EJECTOR.

Whether or not the drying cycle has been used, if the fast exhaust ball valve 60 had been opened, it will remain open until the chamber door is unlocked. As indicated by the WARNING LIGHT ON block in FIG. 6B, at the time that fast exhaust ball valve 60 begins to close, the chamber door is locked so that current flows through switch 124 to warning light 172 and buzzer 174 which provide warning signals. In the preferred embodiment shown in FIG. 7B, the warning signal generated by buzzer 174 persists over a span of 2 minutes. It should be obvious, however, that other warning signals could be selected over differing intervals of time within the spirit and scope of the invention.

The warning signals indicate that the sterilization process has been completed and that the chamber door may be unlocked. Unlocking the door opens switch 124 and terminates the warning signals, as indicated by the TWO MIN. BUZZER INTERRUPTED BY DOOR OPENING and the UNLOCK DOOR blocks.

Referring now to FIG. 8, there is shown a piping diagram according to the present invention. Steam is supplied through a shut-off valve 36, a strainer 38 and a check valve 40 according to principles well-known in the art. The steam then passes through a pressure regulator 42, and the pressure of the steam is monitored by the pressure-sensitive switch 34. This portion of the apparatus corresponds to the decisional block labeled STEAM PRESSURE UP in FIG. 6A. The steam monitored by pressure-sensitive switch 34 passes through steam entry valve 44, which is a solenoid valve, and enters chamber 54, through ball valve 52, and chamber jacket 50. Steam entry valve 44 is shunted by manual by-pass valve 84. Valve 84 provides an alternate path for steam flow to ball valve 52 and chamber jacket 50 should there be an electrical malfunction in the system causing solenoid valve 44 to become inoperative. The steam in chamber jacket 50 flows to steam trap 46 and on to condensor 49. When a full flow of steam is attained, steam trap 46 closes to maintain jacket 50 hot.

Valve 44 controls the flow of steam into chamber 54, through ball valve 52, as well as the flow into jacket 50. Valve 44 is, in turn, controlled by temperature controller and recorder 48. Temperature controller and recorder 48 records the temperature of chamber 54 throughout each cycle of operation, and it regulates the temperature of the steam in chamber 54 by monitoring the temperature in drain 56 and opening and closing valve 44 in response thereto. More specifically, the temperature controller and recorder 48 senses the temperature of the steam in drain 56. In response to the steam temperature inside drain 56, temperature controller and recorder 48 operates valve 44 to control the flow of steam into jacket 50 and chamber 54.

Drain 56 is connected to steam trap 58 through check valve 57. Steam trap 58 maintains the temperature of the steam inside chamber 54 at the set point temperature by closing when chamber 54 is loaded with steam. Steam trap 58, then, maintains saturated steam in the piping between trap 58 and drain 56.

Drain 56 is also connected to fast exhaust ball valve 60 through check valve 57. Fast exhaust ball valve 60 is connected to steam ejector 66, and steam flows from drain 56 to steam ejector 66 when fast exhaust valve 60 is open, that is, when instruments or dressings are being sterilized, see FIG. 6B. Further, drain 56 is connected to slow exhaust ball valve 62 through check valve 57. Slow exhaust ball valve 62 is connected to needle valve 64. Therefore, steam flows from drain 56 to needle valve 64 when slow exhaust valve 62 is open, that is, when a solution is being sterilized, see FIG. 6B. As shown in FIG. 8, steam traps 46 and 58, steam ejector 66, and needle valve 64 are connected to the inlet end of condensor 49.

With fast exhaust ball valve 60 open, steam is exhausted from chamber 54 and ejected by steam ejector 66 to condensor 49. Steam flows through piping 68 and ball valve 70 to operate steam ejector 66. As the steam is exhausted from chamber 54 through ball valve 60, air is drawn into chamber 54 by way of piping 72 and air filter 74.

The water supply for condensor 49 is regulated by valve 76 and water supply solenoid valve 78. In addition, a manual bypass valve 80 is shunted across solenoid valve 78 and a vacuum breaker 82 is connected to valve 78 between valve 76 and valve 78. In the event that the system suffers an electrical power failure, the steam entry valve 44 and water supply valve 78 would be rendered inoperative since they are electrically controlled solenoid valves. Therefore, manual bypass valves 84 and 80 are connected across valves 44 and 78, respectively, in oreder to provide alternative paths for the steam flow.

The pressure of the steam entering chamber 54 through ball valve 52 is monitored by ambient pressure switch 86. Upon completion of the exhaust cycle, see the CYCLE DECISION I loop in FIG. 6B, the chamber pressure must reach ambient pressure before CYCLE DECISION II can be entered. This is characterized by the block designated AMBIENT PRESSURE in FIG. 6B. When the exhaust cycle has been completed, pressure switch 86 will indicate whether chamber 54 is at ambient pressure and, accordingly, whether CYCLE DECISION II can be entered. As previously explained, CYCLE DECISION II determines whether a drying cycle will be initiated.

Steam ejector 66 is used only in the drying cycle. In other words, unless the article being sterilized is a dressing, ball valve 70 is closed and steam ejector 66 is not utilized. However, as shown in FIG. 6B, despite the fact that steam ejector 66 may not be operating, that is, despite the fact that the apparatus by-passes the drying cycle, the fast exhaust ball valve 60 will still be open.

Figure 7A:
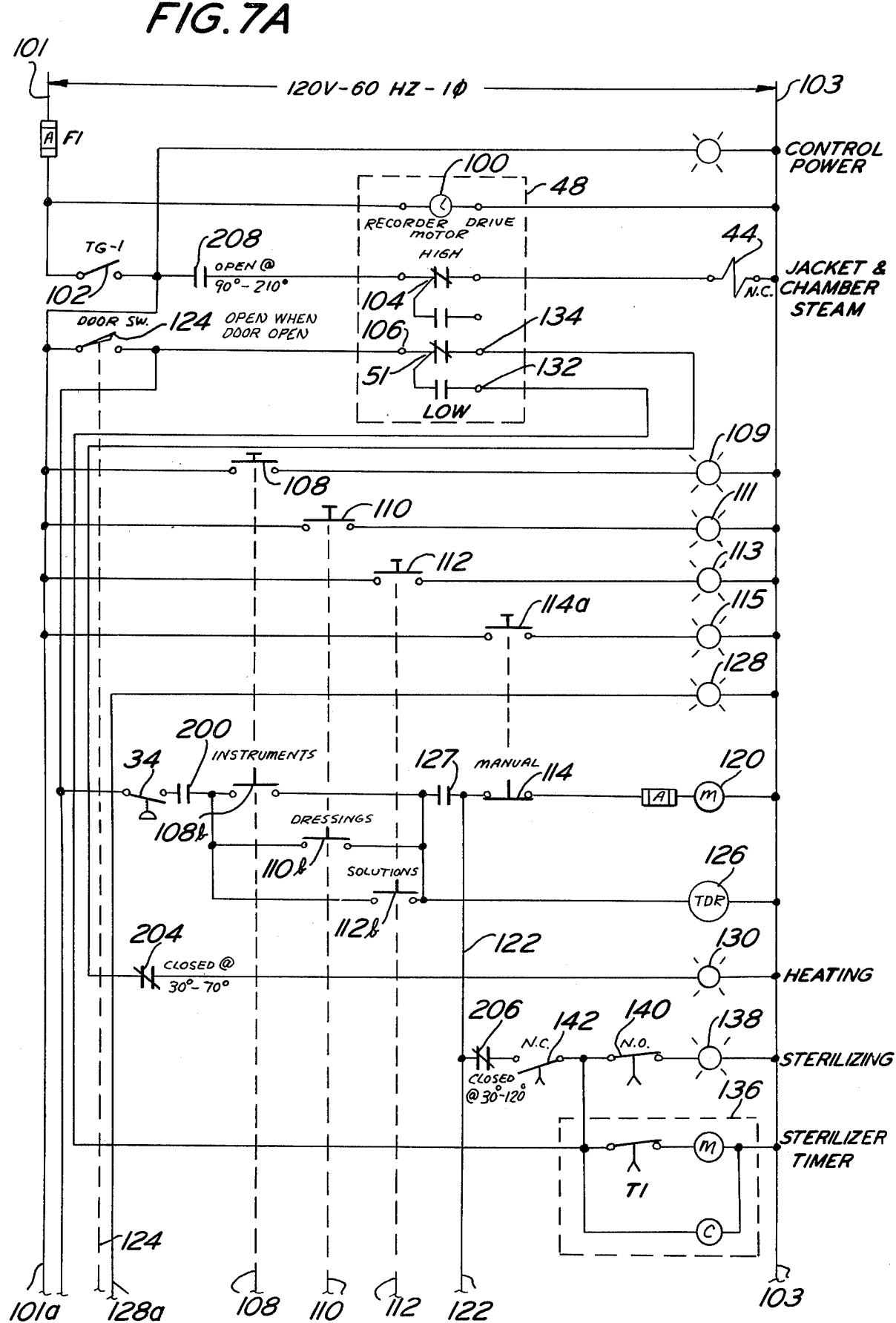
FIG. 7A and 7B comprise a schematic of an electrical circuit in accordance with the present invention.
Figure 7B:
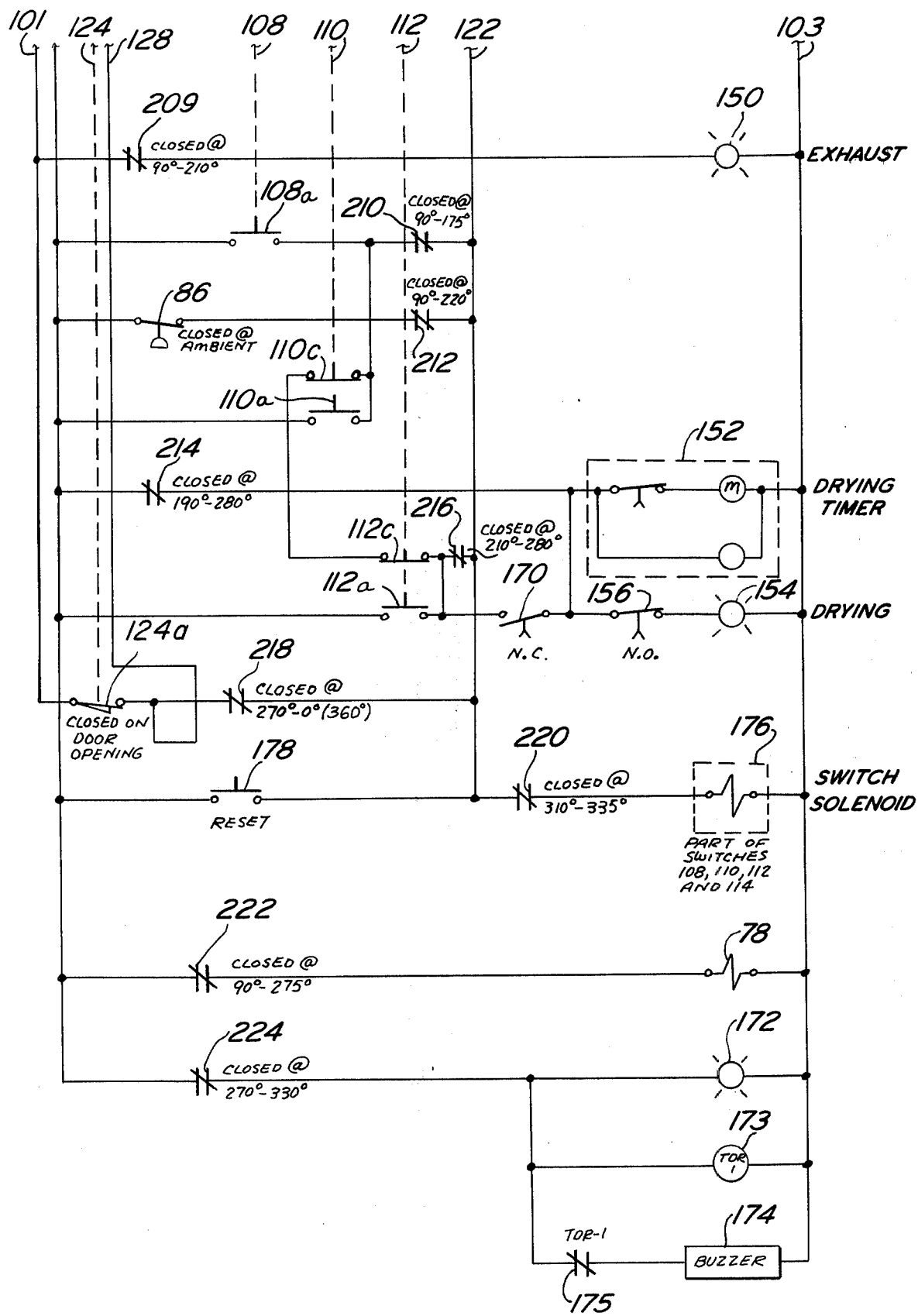

Referring now to FIGS. 7A and 7B, there is shown an electrical schematic for the present invention. Electrical power is supplied to recorder motor 100 in temperature controller and recorder 48 by means of power lines 101 and 103. Temperature sensitive switches 104 and 51, along with motor 100, are part of temperature controller and recorder 48. Temperature switch 104 is connected to solenoid valve 44, toggle switch 102 and microswitch 208. Switch 104 is actuated (opens) at the upper temperature limit (set point temperature + 2° F) while temperature switch 51 is actuated (opens) at the lower temperature limit (set point temperature −2° F).

Figure 1:
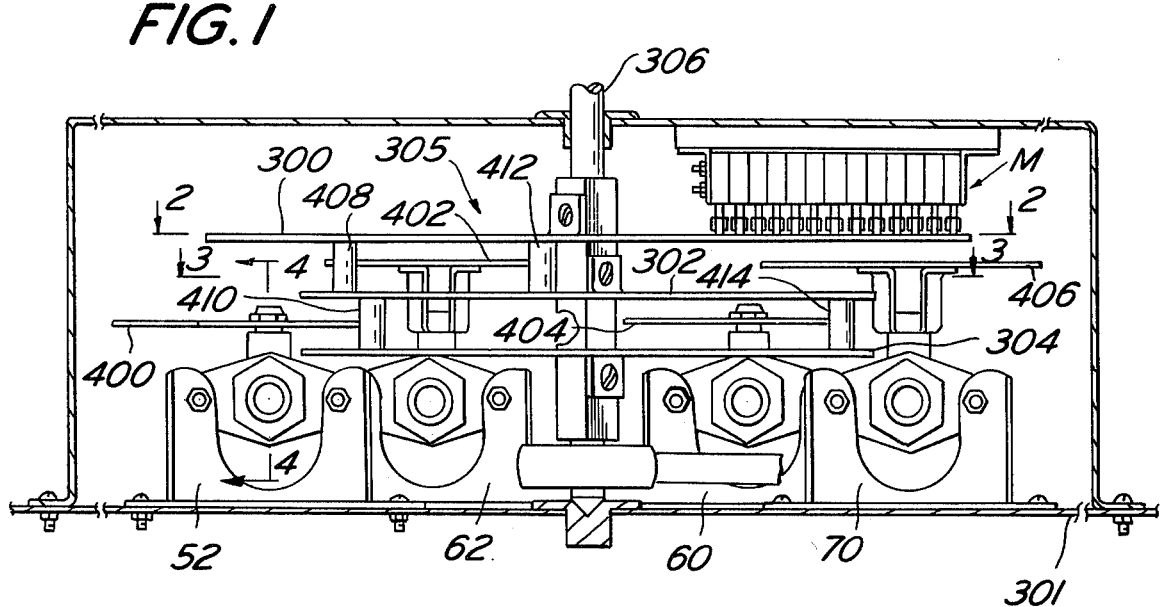
FIG. 1 is a view in side elevation of a sterilizing apparatus constructed in accordance with the principles of the present invention.
Figure 2:
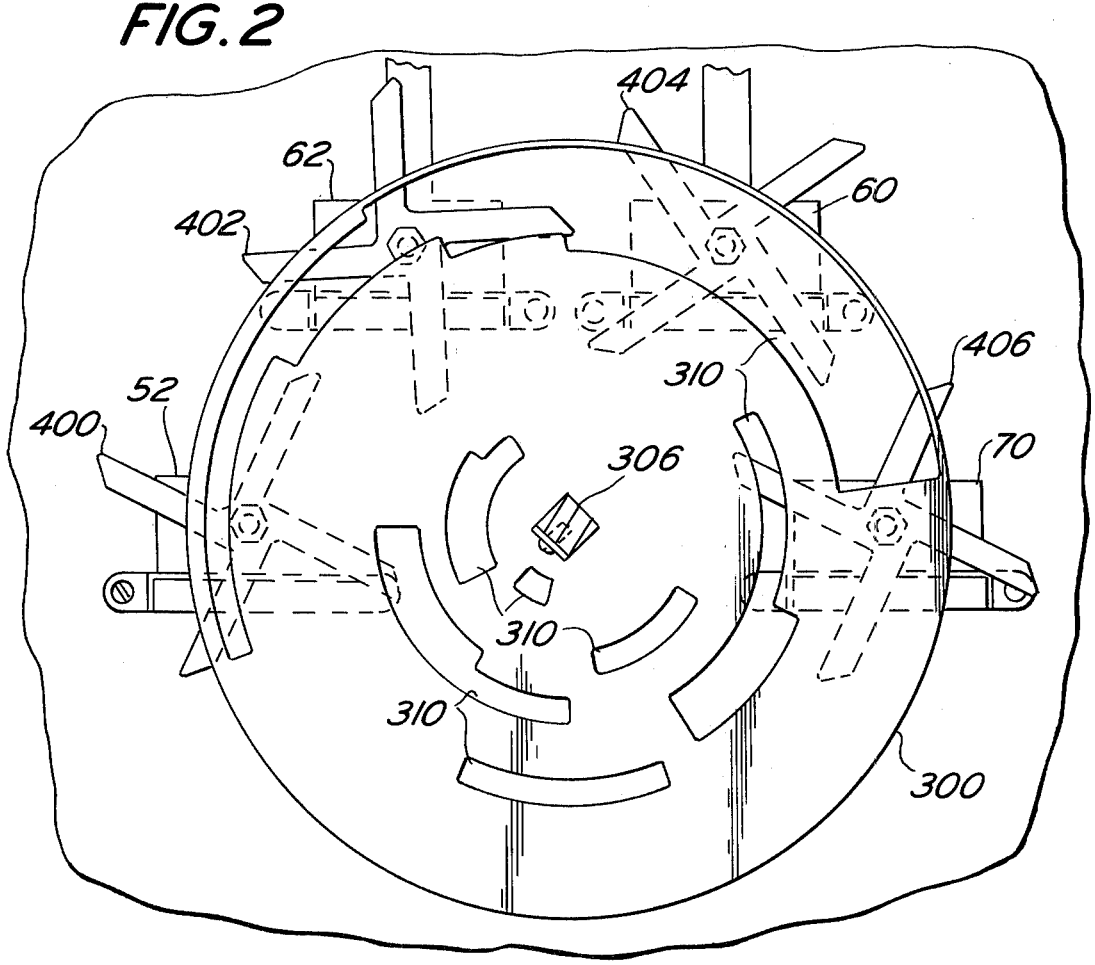
FIG. 2 is a view, partly in cross-section, taken along line 2—2 in FIG. 1.

Push button switches 108, 110, and 112 determine the particular operating cycle for the system, namely, instruments, dressings or solutions, and push button switch 114 determines whether operation is manual or automatic. Specifically, switch 114 is mechanically coupled to switch 114a; so that when switch 114 closes, switch 114a opens. When depressed, switch 114 closes and provides a current path from line 101a to light 115. Additionally, depressing switch 114 causes switch 114a to open so that current cannot flow to motor 120. Thus, with switch 114 depressed, the apparatus must be operated manually. Lights 109, 111 and 113 are illuminated when switches 108, 110, and 112, respectively, are depressed. That is, with switches 108, 110 and 112 depressed, current flows to lights 109, 111 and 113, respectively. Microswitches 200, 204, 206, 208, 209, 210, 212, 214, 216, 218, 220, 222 and 224 are limit switches which are normally open and are operated by a top program disk 300 which is shown in FIGS. 1 and 2. For ease of reference, microswitches 200, 204, 206, 208, 209, 210, 212, 214, 216, 218, 220, 222 and 224 are designated in the aggregate by the letter M. Each of the microswitches M is closed during particular portions of the operating cycles (described in the flow charts appearing in FIGS. 6A and 6B) of the present systems. The on/off states of the microswitches M in relation to the program disk 300 and the operating cycles of the system are displayed in FIG. 9 and discussed in greater detail below.

Microswitches M are controlled by means of top program disk 300. Disk 300 is provided with one or more arcuate slots, designated in the aggregate as 310, at varying radii from the disk center. Circular motion of disk 300 results in intermittent contact between the surface of disk 300 and microswitches M according to the locations and shapes of slots 310. In the automatic mode the disk 300 is driven by motor 120. If the motor 120 is not energized, as in the manual mode with switch 114a open, the disk 300 is rotated manually. The microswitches M control the operation of motor 120 as well as other functions of the apparatus, including the sterilization and drying cycles, as described below. In particular, all microswitches M connected to line 122 control the operation of motor 120, see FIGS. 7A and 7B.

When the steam pressure is above the threshold value, pressure switch 34 closes and power is applied to microswitch 200. If microswitch 200 is closed, the power is applied to push-button switches 108b, 110b and 112b which are electrically connected to time delay relay 126. Push-button switches 108b, 110b, and 112b are mechanically coupled to push-button switches 108, 110 and 112 and to push-button switches 108a, 110a and 112a so that closing switch 108 closes switches 108a and 108b, closing switch 110 closes switch 110a and 110b and opens 110c, and closing switch 112 closes switches 112a and 112b and opens switch 112c. If operation is in the automatic mode, manual switch 114 is not depressed, and switch 114a provides a current path from either switch 108b, 110b or 112b to motor 120. Thus, in the automatic mode, motor 120 drives disk 300, and disk 300 controls the states of the microswitches M.

Figure 9:
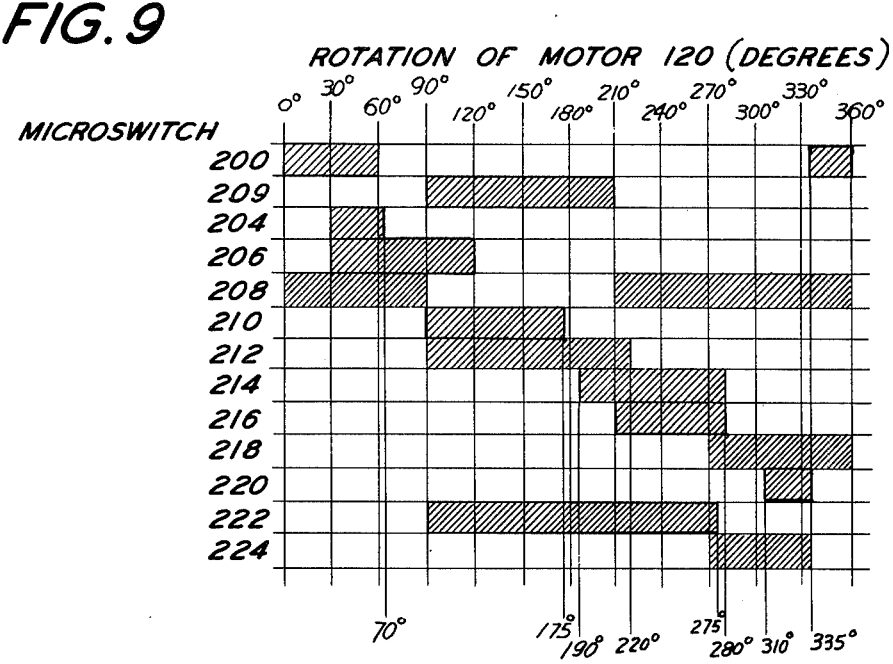
FIG. 9 is a chart showing the states of the microswitches of FIGS. 7A and 7B in relation to the operating cycles of an apparatus in accordance with the present invention.

Referring to FIG. 9, at 0° rotation of disk 300, microswitch 200 is closed. That is, the actuator arm (not shown) of switch 200 extends into an associated one of the slots 310, causing switch 200 to close. Switch 200 remains closed until disk 300 rotates past the 60° mark. At 60° rotation the actuator arm of switch 200 slidably engages the surface of disk 300, and switch 200 opens. Thus, a camming action between the surface of top program disk 300 and the actuator arm of each of the microswitches M controls the on/off state of the microswitch.

As mentioned previously, door switch 124 is mechanically coupled to switch 124a so that closing switch 124 opens switch 124a, see FIG. 7B. Therefore, when the chamber door is closed, switch 124 closes and switch 124a opens. When switch 124a opens, standby light 128 goes off. This corresponds to the operation of the system represented by the block marked LOCK DOOR in FIG. 6A.

With door switch 124, pressure switch 34, microswitch 200, and one of the push-button switches 108b, 110b and 112b closed, the time delay relay 126 is energized. After a 20 second time delay corresponding to the 20 SECOND TIME DELAY block in FIG. 6A, time delay relay 126 closes contacts 127, thereby energizing motor 120 if switch 114a is closed (automatic mode). After 60° rotation of program disk 300, microswitch 200 opens and motor 120 and program disk 300 stop.

Initially, the chamber temperature is below the low temperature limit (set point temperature −2° F.) and temperature-sensitive switch 51 connects terminal 134 to terminal 106. Therefore, closed switch 204 energizes heat light 130. In particular, at 30° rotation of disk 300, microswitch 204 closes and heat light 130 goes on. Heat light 130 stays on until microswitch 204 opens at 70° rotation or switch 51 disconnects terminals 106 and 134. This corresponds to the HEAT LIGHT ON block in FIG. 6A.

Between 0° and 60° of rotation, ball valve 52 is opened by the program disks 302 and 304, see FIGS. 1, 2, 3 and 10. The closing and opening of ball valves 52, 62, 60 and 70 in synchronism with the rotation of program disks 300, 302, and 304 is discussed in detail hereinafter. Ball valve 52, when open, admits steam to chamber 54 as indicated by the ADMIT STEAM block in FIG. 6A. Once the lower temperature limit, viz. 2° F. below the set point temperature, is reached the temperature sensitive switch 51 releases terminal 106 from contact with terminal 134 and connects terminal 106 with terminal 132. As a result, heat light 130 goes off and sterilizer timer 136 is actuated. This is indicated by the ACHIEVE SET POINT TEMP. and START STERILIZER TIMER blocks in FIG. 6A. When sterilizer timer 136 is actuated, switch 142 opens, switch 140 closes and sterilizer light 138 goes on as indicated by the STERILIZER LIGHT ON block.

During sterilization, the chamber temperature is regulated by temperature controller and recorder 48. Temperature controller and recorder 48 includes temperature-sensitive switches 104 and 51 and recorder drive motor 100. If, for any reason, the chamber temperature falls below the lower temperature limit, viz. 2° F. below the set point temperature, temperature-sensitive switch 51 releases terminal 106 from contact with terminal 132 and reconnects terminal 106 to terminal 134. As a result, heat light 130 goes on while sterilizer time 136 is automatically reset due to the disconnection of power thereto. This is indicated by the TEMP. −2° F. FROM SET POINT and RESET TIMER blocks in FIG. 6A. Should, however, the lower temperature limit again be reached, switch 51 disconnects terminal 106 from terminal 134 and reconnects it to terminal 132 to re-energize sterilizer timer 136 which starts to measure a new timing cycle while steam enters chamber 54.

When the chamber temperature is below the upper temperature limit, viz. 2° F above the set point temperature, switch 104 is closed. Microswitch 208 is closed from 0° to 90° rotation of disk 300 so that if switch 104 is closed at this time, solenoid valve 44 is opened and steam flows to chamber jacket 50 and ball valve 52 as indicated by the SOLENOID VALVE STAYS OPEN block. When the chamber temperature exceeds the upper temperatue limit, temperature-sensitive switch 104 opens causing solenoid valve 44 to close and shut off the flow of steam to jacket 50 and ball valve 52 as indicated by the CLOSE SOLENOID VALVE block.

When the timing cycle measured by sterilizer timer 136 ends, switch 140 opens, sterilizer light 138 turns off, and switch 142 closes to provide a current path to microswitch 206. This corresponds to the END OF STERILIZE TIME block in FIG. 6A. Microswitch 206 is closed from 30° to 120° of rotation of program disk 300 so that power is transmitted to motor 120 at this time to advance it to the 120° position once the sterilizer timer cycle is over.

When microswitch 206 opens at 120° rotation of the disk 300, it cuts off power to motor 120. The motor 120 will stop at this point unless power is supplied to it from an alternate current path. In the instruments or dressings mode of operation, however, push-button switch 108a or 110a is closed. In addition, from 90° to 175° rotation of disk 300 microswitch 210 is closed, see FIG. 9. Since microswitch 210 is closed from 90° to 175°, there is an alternate path of power to motor 120 through switch 108a or 110a and switch 210 when, at 120°, microswitch 206 opens. Further, microswitch 210 remains closed until disk 300 rotates to 175°. At 175°, in the instruments or dressing mode, fast exhaust valve 60 is open and switch 210 opens and cuts off power to motor 120. In the instruments or dressings mode, then, motor 120 must stop at 175° unless an alternate current path is provided to motor 120.

At 90°, microswitch 209 closes, exhaust light 150 goes on, and the system enters CYCLE DECISION I in FIG. 6B. In the instruments and dressings modes, switches 112 and 112a are not depressed. In addition, in the instruments mode, switches 108 and 108a are depressed while switches 110 and 110a are not. Therefore, in the instruments mode, a current path is provided through switches 108a, 110c and 112c to microswitch 216. Microswitch 216, however, is open until 210° so that no current flows through switch 216 at 175°. Similarly, in the dressings mode, switch 110c is depressed so no current flows through switch 216 at 175°. Thus, in the instruments and dressings modes, the motor 120 is stopped at 175° while chamber 54 is exhausted of steam in the fast exhaust mode. This is indicated by the FAST EXHAUST VALVE OPEN block. When the chamber pressure drops to ambient pressure, however, pressure-sensitive switch 86 closes, and motor 120 is energized since microswitch 212 is closed at 175°, see FIG. 9. And switch 212 keeps motor 120 energized up to 220°.

In comparison, if the solution mode is selected, no power flows through microswitch 210 despite the fact that it is closed from 90° to 175° rotation, since neither switches 108a nor 110a are depressed. At 70° rotation, as mentioned previously, switch 204 opens maintaining the heat light 130 off. At 90°, microswitch 209 closes, energizing exhaust light 150 and the system enters CYCLE DECISION I. Over the 120° interval of rotation extending from 90° to 210°, microswitch 209 remains closed and exhaust light 150 remains on.

At 120°, switch 206 opens cutting off power to motor 120 unless an alternate current path to motor 120 is provided. While ball valve 52 remains open, steam is not permitted to enter chamber 54. This is caused by closing solenoid valve 44 when microswitch 208 is opened at 90° to 210°. Thus steam is slowly exhausted from jacket 50 through ball valve 52 to chamber 54. Slow exhaust valve 62 is open at 120° rotation of disk 300, as indicated by the SLOW EXHAUST VALVE OPEN block, and the motor 120 remains stopped at 120° rotation in the slow exhaust mode until ambient pressure is reached in chamber 54. When ambient pressure is reached, pressure sensitive switch 86 closes and power is supplied to motor 120 through switch 212. The motor 120 advances to 210°, and at 210° switch 216 closes keeping motor 120 energized since switch 112a is depressed in the solutions mode. At 220° switch 212 opens, but power is still supplied to motor 120 through switch 216.

As disk 300 passes 210°, switch 209 opens and exhaust light 150 turns off. Meanwhile, microswitch 214 closes at 190° actuating drying timer 152 which closes switch 156, turning on drying light 154, and opens switch 170. In the instruments mode, motor 120 is energized up to 280° by means of switch 216, switch 112c, switch 110c and switch 108a. In the solutions mode, power is applied to motor 120 up to 280° by means of switch 112a and 216. Thus, in the instruments and solutions modes, the drying cycle is bypassed, see FIG. 6B, and motor 120 rotates straight through to 280°.

In contrast, in the dressings mode, no power is applied to switch 216 through switch 110c so that when switch 212 opens at 220° no power is supplied to motor 120 unless an alternate current path to motor 120 is provided. As mentioned previously, switch 214 closes at 190°, actuating drying timer 152. Drying timer 152, when actuated, opens switch 170 so current cannot flow through switch 170 to switch 216. Motor 120, then, remains stopped at 220° in the dressings mode while the system runs through the drying cycle.

Once drying timer 152 completes its cycle, it opens switch 156, which turns off drying light 154, and closes switch 170. Accordingly, power is transferred through switch 214 to switches 170 and 216 up to 280°. Motor 120 and disk 300, then, are driven to 280° rotation.

At 270° microswitch 224 closes and, accordingly, warning light 172, time delay relay 173, and buzzer 174 go on. At the end of a predetermined interval, time delay relay 173 times out closing contacts 175, and buzzer 174 goes off. Warning light 172 stays on until switch 224 opens at 330°. From 90° to 275°, microswitch 222 closes so that solenoid valve 78 conducts water to condensor 49 during the exhaust and drying cycles.

Since microswitch 218 is closed at 280° and switch 124a closes when the chamber door is opened, power is delivered to motor 120 as the door opens. The causes the motor 120 to drive the disks 300, 302 and 304 to their starting positions.

Finally, microswitch 220 closes when disk 300 rotates past 310°. When closed, microswitch 220 operates latch relay 176, which is part of switches 108, 110, 112 and 114, so as to release switches 108, 110, 112 and 114 when switch 124a closes upon opening the chamber door. As indicated in FIG. 7B, however, this may also be accomplished by manually depressing reset switch 178 with the chamber door closed and cycling motor 120 through one revolution.

Referring now to FIGS. 1 through 5 and 10, there is shown in detail the structure of the program disk 300 and the ball valves 52, 62, 60 and 70 of the present invention. In particular, in FIG. 1 there is shown a motor drive shaft 306 which is coupled to motor 120. Disks 300, 302 and 304 are mounted on shaft 306. Top program disk 300 contacts the plurality of microswitches 200, 204, 206, 208, 209, 210, 212, 214, 216, 218, 220, 222 and 224, previously described and designated in the aggregate as M. Immediately below top program disk 300 is middle program disk 302, and located beneath disk 302 is bottom program disk 304. Disks 302 and 304 are of equal diameters and are mounted concentrically on shaft 306. All of the disks may herein be referred to in the aggregate as disks 305. Disks 305 are variously joined near their edges by program posts 408, 410, 412, and 414. Top program disk 300 is also mounted concentrically on shaft 306. However, top disk 300 is of greater diameter than disks 302 and 304. Furthermore, as shown in FIG. 2, program disk 300 is provided with arcuate slots, designated generally as 310, at various angles and radii from the disk center which coincides with shaft 306. Disk 300 is joined to middle disk 302 by means of program posts 408 and 412.

The top program disk 300 is provided with slots 310 of varying lengths and at different locations along the face of the disk to provide a camming surface to operate microswitches M. Slots 310 cooperate with microswitches M in a camming arrangement, switching certain of the microswitches M on and off at predetermined times. Thus, each of the microswitches M remains in the closed position for the duration of the time interval required by the disk 300 to traverse the length of the corresponding arcuate slot 310. That is, the actuator arm (not shown) of each of the switches M protrudes beneath the top surface of disk 300 and into an associated one of the slots 310 for a predetermined time period corresponding to the length of the slot 310, causing that switch to close during that time period. Upon traversing the entire length of the arcuate slot 310, the actuator arm is placed in sliding contact with the solid surface of disk 300. As the actuator arm slides over the surface of disk 300, the physical force exerted by disk 300 on the actuator arm causes the switch to open. Cast in other terms, each of the switches M follows the camming surface presented by revolving disk 300 and switches on and off accordingly.

As disk 300 rotates through a full 360°, the system passes through each of the states set forth in the flow charts appearing in FIGS. 6A and 6B. Referring to FIG. 9, depending upon the length of each of the slots 310, each of the switches M remains closed for a fixed portion of a full revolution. Therefore, each of the microswitches M is on or off according to the portion of a full revolution traveled by disk 300. For example, microswitch 206 is closed from 30° to 120° or one-quarter of a full revolution of disk 300 and, accordingly, the length of the arcuate slot 310 which passes beneath microswitch 206 is 90° long. Similarly, microswitch 200 is open from 60° to 335° so that the length of the arcuate slot 310 which corresponds to microswitch 200 is 360° minus 275° or 85° long.

Referring to FIG. 7A, it will be noted that motor 120 is alternately energized as previously described by a variety of the microswitches M which connect to wiring 122. In turn, the microswitches M are opened and closed by arcuate slots 310 so that the arcuate slots 310 control the synchronous energization of motor 120.

Figure 3:
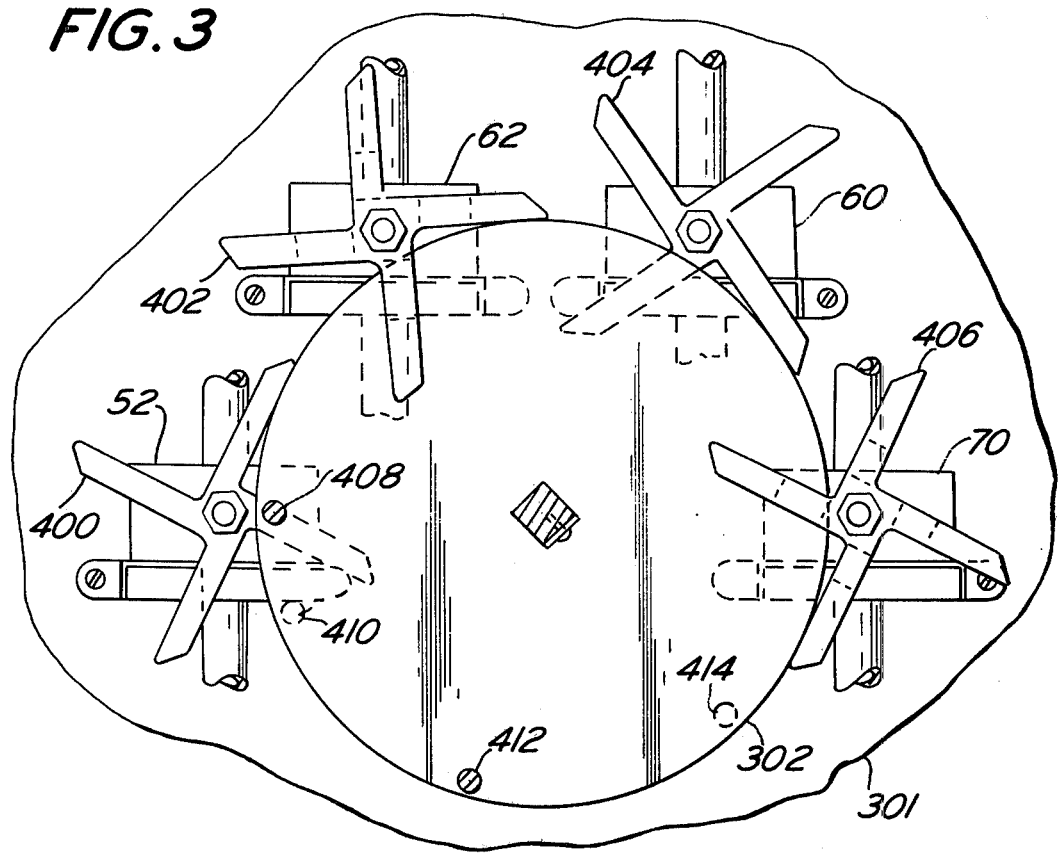
FIG. 3 is a view, partly in cross-section, taken along line 3—3 in FIG. 1.

To complete a full cycle of operation, the mechanical components shown in FIG. 8 must be synchronized with the electrical elements shown in FIGS. 7A and 7B. More specifically, the operation of the ball valves 52, 70, 62 and 60 must be synchronized with the movement of the arcuate slots 310 in disk 300, disk 300 being driven by motor 120. For this purpose, the assembly of disks 300, 302 and 304 is provided with a plurality of program posts 408, 410, 412, and 414, as shown in FIG. 3. The position of each of the program posts is designed to enable each of the ball valves to operate in synchronism with the operation of the microswitches M by slots 310. Program posts 408 and 412 join disks 300 and 302, see FIG. 1, and program 410 and 414 join disks 302 and 304.

Figure 4:
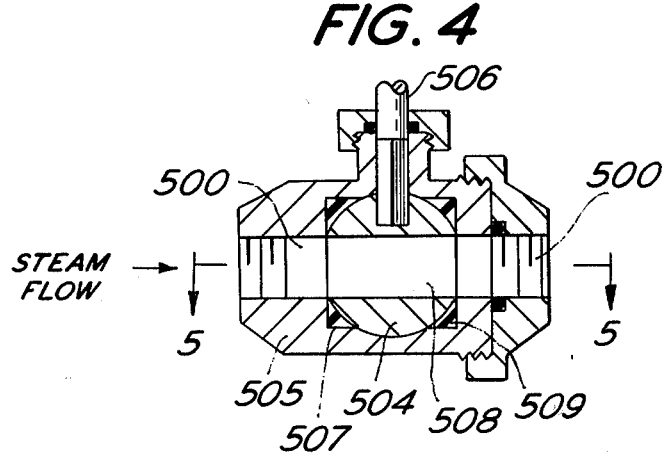
FIG. 4 is a cross-sectional view of a ball valve taken along the line 4—4 in FIG. 1.

As shown in FIG. 3, each ball valve is mounted on a base 301 and located at a preselected position along the periphery of disks 300, 302 and 304. Focusing, for purposes of explanation, on ball valve 52, it will be noted that ball valve 52 is provided with paddle arms 400. The detailed structure of ball valve 52 is shown in FIG. 4. There, it is shown that ball valve 52 includes a ball valve member 504 which securely engages a stem 506. The stem 506 securely engages ball valve member 504 so that rotation of stem 506 about its own axis causes ball valve member 504 to rotate about the same axis. The ball valve member 504 is spherical in shape and is provided with a flow passage 508. Additionally, ball valve member 504 is housed within valve housing 505 which is provided with a flow passage 500. The ball valve member 504 is kept in position by annular seats 507 and 509 located at each end of flow passage 508, between the ball valve member 504 and the valve housing 505. Paddle arms 400 securely engage the stem 506 so that circular displacement of the paddle arms causes stem 506 to rotate about its own axis. Thus, stem 506 and the ball 504 are rotated by circular motion of the paddle arms 400 to bring flow passages 500 and 508 into and out of alignment.

Ball valve assemblies are commonly provided with a stop post permitting only 90° of motion. This stop post has been removed in the present invention to permit stem 506 and ball valve 504 a full 360° rotation. By positioning the ball valves sufficiently close to the disks 300, 302 and 304 full 360° rotation of the ball valve member 504 is achieved when paddle arms 400, 402, 404 and 406—corresponding respectively to ball valves 52, 62, 60 and 70—are contacted by program posts 408, 410, 412, and 414. Furthermore, the relative position of each of the ball valves 52, 62, 60 and 70 with respect to the slots 310 determines the synchronous rotation of ball valve member 504 with the on/off states of microswitches M.

The structure shown in FIG. 4 describes ball valves 62, 60 and 70 as well as ball valve 52. In the preferred embodiment shown in FIG. 1, ball valves 52 and 60 are provided with paddle arms 400 and 404 which extend into the space separating disks 302 and 304. On the other hand, ball valves 62 and 70 are provided with paddle arms 402 and 406 which are disposed at heights higher than the height of paddle arms 400 and 404. More specifically, paddle arms 402 and 406 extend into the space separating disks 300 and 302 rather than the space separating disks 302 and 304. Consequently, program posts 410 and 414, which do not enter the space between disks 300 and 302, do not control the operation of ball valves 62 and 70 since they cannot contact paddle arms 402 and 406 of those ball valves. On the other hand, program posts 408 and 412 serve to control the operation of the ball valves 62 and 70 since these program posts extend into the space separating disks 300 and 302. In other words, program posts 408 and 412 are capable of contacting the paddle arms 402 and 406 during the course of a full revolution of shaft 306 and disks 300, 302 and 304 mounted thereon.

Figure 10:
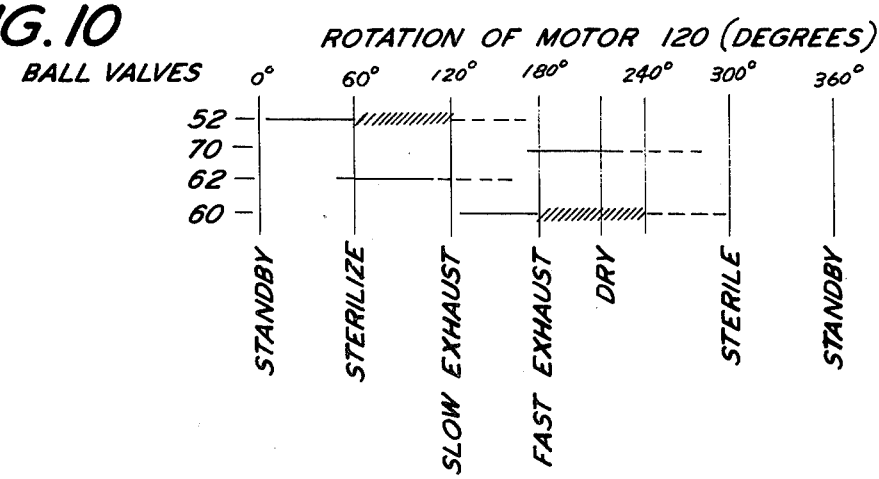
FIG. 10 is a chart showing the opening or closing of the ball valves according to the operating cycles of the present invention.

The synchronous relationship of the microswitches M and the ball valves 52, 62, 60 and 70 is disclosed in FIGS. 9 and 10. Thus, for example, as the drive shaft 306 begins to rotate, the actuator arm of microswitch 200 projects into the space provided by an associated arcuate slot 310. At this point, none of the ball valves 52, 62, 60 or 70 is open and the system is in the standby mode. As shaft 306 passes through 60° rotation, microswitch 200 traverses the entire length of the associated arcuate slot 310 and its actuator arm then slidably contacts the top surface of disk 300. Accordingly, microswitch 200 is switched to the off or open state by the solid surface of disk 300. Traveling from 0° to 60°, program post 410 contacts paddle arms 400 mounted on ball valve 52 bringing flow passages 500 and 508 into alignment. Consequently, ball valve 52 "opens". Further revolution of paddle arms 400 due to contact with program post 414 causes flow passages 500 and 508 to go out of alignment so that ball valve 52 "closes". That is, the opening and closing of ball valve 52 by means of contact between paddle arms 400 and program post 410 is gradual based on the gradual alignment of flow passages 500 and 508. Ball valves 62, 60 and 70 are opened and closed in an indentical manner.

Figure 5:
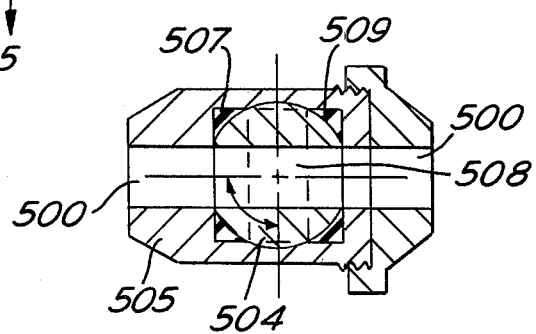
FIG. 5 is a cross-sectional view of a ball valve taken along the line 5—5 of FIG. 4.

The gradual opening and closing of a ball valve is diagrammatically illustrated in FIG. 10 where solid lines indicate the gradual opening of a valve, dotted lines indicate the gradual closing of a valve, and hatched lines indicate that a valve is full open. Ball valve 52 is closed initially but opens as paddle arms 400 causes valve stem 506 and ball valve member 504 to rotate due to contact with program post 410. After nearly 60° of rotation of disks 305, paddle arms 400 are turned sufficiently to cause ball valve member 504 to align flow passages 508 and 500, as shown in FIGS. 4 and 5. FIGS. 4 and 5 show the extreme alignment (FIG. 4) and (FIG. 5) of flow passages 500 and 508. Alignment of flow passages 500 and 508 as shown in FIG. 4 permits the maximum flow of steam through a ball valve. Further rotation of the paddle arms 400, however, results in the rotation of stem 506 and ball valve member 504 so that flow passages 500 and 508 fall increasingly out of alignment. Consequently, the flow through ball valve 52 gradually decreases until, at nearly 180° rotation of disks 305, the steam flowing through the inlet end of flow passage 500 cannot enter flow passage 508.

As shown in FIG. 10, it is possible for a ball valve to remain in the state of maximal alignment (FIG. 4) of flow passages 500 and 508 for finite periods of time. Thus, for example, ball valve 52 achieves maximum steam flow at 60° and retains that position until 120°, at which point the program post 414 rotates paddle arms 400 so that flow passages 500 and 508 fall increasingly out of alignment.

In the preferred embodiment shown, the diameters of the flow passages 500 and 508 are such that the transition of the ball valve 52, 62, 60 or 70 from its "off" state (with no flow) to its "on" state (with maximal flow) requires approximately 60° rotation of the shaft 306. However, as will be obvious to one of ordinary skill in the art, the diameters of flow passages 500 and 508 may be varied to produce other intervals over which the valve turns completely on or off.

Since the present invention is directed towards a method and apparatus for sterilizing articles such as instruments, dressings, and solutions it is important that the flow of steam — upon which the sterilization process hinges — be reliably and accurately regulated. For this purpose, valves 52, 70, 62 and 60 are all ball valves having the structure shown in FIGS. 4 and 5. The primary advantages of such a ball valve are that it is relatively free from the effects of particles and the corrosive effects of steam which are commonly found in other types of valves. In particular, the rotation of ball valve member 504 in valve housing 505 produces a wiping action which reduces or eliminates the effects of corrosion or foreign particles in the steam. This is a significant advantage over the use of poppet valves.

In summary, sterilization of liquid or solid matter is accomplished by synchronizing the operation of ball valves 52, 70, 62 and 60 with the operation of microswitches M by means of relative motion between switches M and a program disk 300 and by means of the rotation of ball valve paddle arms 400, 402, 404 and 406 by program posts 408, 410, 412, and 414. The program posts are fixed with respect to the program disks so that the operations of microswitches M and paddle arms 400, 402, 404 and 406 are synchronous.

The present invention may be embodied in other specific forms without departing from the spirit or essential attributes thereof and, accordingly, reference should be made to the appended claims, rather than to the foregoing specification as indicating the scope of the invention.

We claim:

1. A method for sterilizing an article in a chamber operatively connected to a plurality of ball valves provided with rotary means for opening and closing said ball valves, comprising:
    programming a disc having a plurality of posts depending therefrom by providing said disc with a plurality of slots;
    rotating said programmed disc in slidable contact with a plurality of switches to cause said switches to open and close in a predetermined sequence determined by said slots and to cause said posts to contact said ball valve rotary means to open and close said ball valves in a predetermined sequence determined by said posts;
    admitting a gaseous sterilizing agent to said chamber;
    maintaining the temperature of said sterilizing agent in said chamber within a preselected range of a set point temperature for a predetermined interval of time;
    exhausting said sterilizing agent from the chamber and
    controlling the sequence and duration of said admitting, maintaining and exhausting steps in response to said predetermined sequence in which said switches are opened and closed and said posts contact said rotary means in response to said rotation of said programmed disc.

2. A method in accordance with claim 1 wherein said article is a dressing and including the step, following the exhausting step and carried out in said chamber, of drying said article of condensed moisture.

3. A method in accordance with claim 1 wherein said temperature maintaining step includes the steps of admitting said sterilizing agent to said chamber if said sterilizing agent temperature in said chamber drops below an upper temperature limit and preventing said sterilizing agent from entering said chamber if said sterilizing agent temperature in said chamber rises above said upper temperature limit, and selectively re-initiating said temperature maintaining step if said sterilizing agent drops below a lower temperature limit.

4. A method of sterilizing an article in a chamber operatively connected to a plurality of ball valves having rotary means for opening and closing said ball valves, comprising:
    providing a slotted disc having a plurality of posts depending therefrom in rotatable contact with one or more of said ball valve rotary means;
    providing an electric control circuit including a timer and a plurality of switches in slidable contact with said disc;
    rotating said slotted disc to cause said switches to operate said electrical control circuit in a predetermined sequence of states and to cause said posts to rotatably contact each of said ball valve rotary means to operate said ball valves in a predetermined sequence of states;
    admitting a gaseous sterilizing agent to said chamber by opening at least one of said ball valves;
    maintaining the temperature of said sterilizing agent in said chamber within a preselected range of a set point temperature for a predetermined interval of time determined by said timer;
    exhausting said sterilizing agent from said chamber and
    controlling the sequence and duration of said admitting, temperature maintaining, and exhausting steps according to the operation of said electrical control circuit and the operation of said ball valves in response to said rotating step.

5. A method in accordance with claim 1 wherein said article is a dressing and including the step, following the exhausting step and carried out in said chamber, of drying said article of condensed moisture.

6. A method in accordance with claim 4 wherein said temperature maintaining step includes the steps of admitting said sterilizing agent to said chamber if said sterilizing agent temperature in said chamber drops below an upper temperature limit and preventing said sterilizing agent from entering said chamber if said sterilizing agent temperature in said chamber rises above said upper temperature limit, and selectively re-initiating said temperature maintaining step if said sterilizing agent drops below a lower temperature limit.

* * * * *